(12) United States Patent
Erbel et al.

(10) Patent No.: US 9,730,654 B2
(45) Date of Patent: Aug. 15, 2017

(54) DETECTION OF THE POSITION OF A MOVING OBJECT AND TREATMENT METHOD

(75) Inventors: Stephan Erbel, München (DE);
Kajetan Berlinger, München (DE);
Armin Fürst, Kirchheim (DE)

(73) Assignee: Brainlab AG, Munich (DE)

( * ) Notice: Subject to any disclaimer, the term of this patent is extended or adjusted under 35 U.S.C. 154(b) by 748 days.

(21) Appl. No.: 13/354,843

(22) Filed: Jan. 20, 2012

(65) Prior Publication Data

US 2012/0123251 A1 May 17, 2012

Related U.S. Application Data

(62) Division of application No. 12/333,556, filed on Dec. 12, 2008, now Pat. No. 8,391,955.
(Continued)

(30) Foreign Application Priority Data

Dec. 13, 2007 (EP) .................................... 07150014

(51) Int. Cl.
*A61B 6/04* (2006.01)
*A61B 6/02* (2006.01)
(Continued)

(52) U.S. Cl.
CPC ............ *A61B 6/0492* (2013.01); *A61B 6/025* (2013.01); *A61N 5/1049* (2013.01);
(Continued)

(58) Field of Classification Search
CPC ............ A61B 6/00; A61B 6/03; A61B 6/0492; A61B 6/025; G06T 7/33; G06T 7/246;
(Continued)

(56) References Cited

U.S. PATENT DOCUMENTS 6,144,875 A * 11/2000 Schweikard ......... A61N 5/1049
378/69
7,204,640 B2 4/2007 Fu et al.
(Continued)

FOREIGN PATENT DOCUMENTS

WO 2006/121164 11/2006

OTHER PUBLICATIONS

Maurer, "4D Digital Tomosynthesis for the On-Board Analysis of Respiratory Induced Motion Effects", International Journal of Radiation: Oncology Biology Physics, vol. 69, No. 3, Oct. 2007, p. S631.
(Continued)

*Primary Examiner* — Peter Luong
(74) *Attorney, Agent, or Firm* — Tucker Ellis LLP (57) ABSTRACT

The invention relates to a method for determining the position of an object moving within a body, wherein the body is connected to markers, a movement signal is determined based on the measured movement of the markers, images are taken from the object using a camera or detector, wherein the camera or detector is moved with respect to the object, it is determined from which direction or range of angles or segment the most images corresponding to a predefined cycle of the movement signal are taken, and using at least some or all of the images of the segment containing the most images for a specified movement cycle, an image of the object is reconstructed.

11 Claims, 10 Drawing Sheets

Related U.S. Application Data (60) Provisional application No. 61/016,024, filed on Dec. 21, 2007.

(51) Int. Cl.
*A61N 5/10* (2006.01)
*G06T 7/00* (2017.01)
*G06T 11/00* (2006.01)
*G06T 7/33* (2017.01)
*G06T 7/246* (2017.01)

(52) U.S. Cl.
CPC ............ *G06T 7/0012* (2013.01); *G06T 7/246* (2017.01); *G06T 7/33* (2017.01); *G06T 11/008* (2013.01); *A61N 5/1065* (2013.01); *A61N 2005/1051* (2013.01); *A61N 2005/1059* (2013.01); *G06T 2207/10048* (2013.01); *G06T 2207/10076* (2013.01); *G06T 2207/10112* (2013.01); *G06T 2207/10124* (2013.01); *G06T 2207/30096* (2013.01); *G06T 2207/30204* (2013.01); *G06T 2211/412* (2013.01)

(58) Field of Classification Search
CPC ............... G06T 7/0012; G06T 11/008; G06T 2207/10076; G06T 2207/10112; G06T 2207/10124; G06T 2207/30096; G06T 2207/30204; G06T 2207/10048; G06T 2211/412; A61N 5/1049; A61N 5/1065; A61N 2005/1059; A61N 2005/1051
USPC .................................. 600/407, 425
See application file for complete search history.

(56) References Cited

U.S. PATENT DOCUMENTS

| | | | |
|---|---|---|---|
| 7,260,426 | B2 | 8/2007 | Schweikard et al. |
| 2003/0018245 | A1* | 1/2003 | Kaufman ............... A61B 5/411 600/407 |
| 2005/0054916 | A1 | 3/2005 | Mostafavi |
| 2005/0111714 | A1* | 5/2005 | Shen et al. .................... 382/128 |
| 2005/0201509 | A1 | 9/2005 | Mostafavi et al. |
| 2006/0067473 | A1 | 3/2006 | Eberhard et al. |
| 2007/0025509 | A1 | 2/2007 | Pang et al. |
| 2007/0201613 | A1 | 8/2007 | Lu et al. |
| 2007/0237290 | A1 | 10/2007 | Mostafavi |
| 2009/0129556 | A1* | 5/2009 | Ahn ........................ A61B 6/04 378/208 |

OTHER PUBLICATIONS

Khamene et al., "A Novel Image Based Verification Method for Respiratory Motion Management in Radiation Therapy", Computer Vision, 2007, pp. 1-7.

Murase et al., "Moving object recognition in eigenspace representation: gait analysis and lip reading", Pattern Recognition Letters, vol. 17, No. 2, Feb. 1996, pp. 155-162.

Schweikard et al., "Fiducial-Less Respiration Tracking in Radiosurgery", Lecture Notes in Computer Science, vol. 3217, Jan. 2004, pp. 992-999.

U.S. Appl. No. 10/652,786, filed Aug. 29, 2003 (cited on p. 2 of the specification).

* cited by examiner

Inhaled (Bin 1)
Nearly inhaled (Bin 2)
Intermediate 1 (Bin 3)
Intermediate 2 (Bin 4)
Nearly exhaled (Bin 5)
Exhaled (Bin 6)

Fig. 3C    Tomographic image plane

No match

Fig. 5B

No match

Fig. 5C

Match    Diaphragm

Beam-On Area

Chasing Area

DETECTION OF THE POSITION OF A MOVING OBJECT AND TREATMENT METHOD

RELATED APPLICATION DATA

This application is a divisional application of U.S. application Ser. No. 12/333,556 filed on Dec. 12, 2008, now U.S. Pat. No. 8,391,955, which claims priority of U.S. Provisional Application No. 61/016,024 filed on Dec. 21, 2007, each of which is incorporated herein by reference in its entirety.

BACKGROUND OF THE INVENTION

The present invention relates generally to the detection of the position or state of a moving object, preferably the detection of the position of an object moving within a body, such as for example the position of an organ or a tumor within a patient. The invention relates especially to image sequence matching for respiratory state detection, which can be used for extracranial radiosurgery.

The invention relates also to the determination of the respiratory state by matching a pair or series of x-ray images, which are for example taken during free-breathing, to a corresponding 4D volume scan.

To apply radiosurgical methods to tumors in the chest and abdomen, it is necessary to take into account respiratory motion, which can move the tumor by more than 1 cm. It is known to use implanted fiducials to track the movement of the tumor.

It is also known to track the movement of tumors without implanted fiducials. Reference is made to K. Berlinger, "Fiducial-Less Compensation of Breathing Motion in Extracranial Radiosurgery", Dissertation, Fakultät für Informatik, Technische Universität München; K. Berlinger, M. Roth, J. Fisseler, O. Sauer, A. Schweikard, L. Vences, "Volumetric Deformation Model for Motion Compensation in Radiotherapy" in Medical Image Computing and Computer-Assisted Intervention-MICCAI 2004, Saint Malo, France, ISBN: 3-540-22977-9, pages 925-932, 2004 and A. Schweikard, H. Shiomi, J. Fisseler, M. Dötter, K. Berlinger, H. B. Gehl, J. Adler, "Fiducial-Less Respiration Tracking in Radiosurgery" in Medical Image Computing and Computer-Assisted Intervention-MICCAI 2004, Saint Malo, France, ISBN: 3-540-22977-9, pages 992-999, 2004.

U.S. Pat. No. 7,260,426 B2 discloses a method and an apparatus for locating an internal target region during treatment without implanted fiducials. The teaching of U.S. Pat. No. 7,260,426 B2 with respect to a radiation treatment device, as illustrated in FIG. 1 of U.S. Pat. No. 7,260,426 B2, and with respect to a real-time sensing system for monitoring external movement of a patient, is herewith included in this application.

U.S. application Ser. No. 10/652,786 discloses an apparatus and a method for registering 2D radiographic images with images reconstructed from 3D scan data.

It is known to place external markers, such as IR-reflectors or IR-emitters, on a patient. The markers can be tracked automatically with known optical methods at a high speed to obtain a position signal, which can for example be a breathing signal or a pulsation signal, being indicative of for example the respiratory state.

However, the markers alone cannot adequately reflect internal displacements caused for example by breathing motion, since a large external motion may occur together with a very small internal motion, and vice versa.

SUMMARY OF THE INVENTION

It is an object of the invention to provide a method and an apparatus for determining the position of a moving object, such as for example a tumor, within a body, such as for example a patient. The movement of the object within the body can e.g. be caused by respiratory motion.

This object is solved by the method and the apparatus as defined in the independent claims. Preferred embodiments are defined in the dependent claims.

A method and an apparatus for detecting the state of a moving body or object, such as for the detection of the respiratory state and the corresponding position of an object moving within the body, is presented.

The method can involve the use of a first dataset, such as a plurality or series of first images that each show an internal volume of the body, preferably including the internal object or target region. The plurality or series of first images can for example be a sequence of computer tomography (CT) images each including three-dimensional information about the body and/or the object. A series of 3D CT data sets or images covering a specific period, such as e.g. at least one breathing cycle, is hereinafter referred to as a 4D CT.

Each 3D CT can be segmented to obtain information about for example the position and/or outline and/or surface of an object, such as tumor, within the body or patient. Using a series of segmented 3D CTs, the movement of the object in the first dataset can be determined.

The problem is that the object or tumor moves probably at a time later than that of acquiring the first dataset within the body in a (slightly) different way due to e.g. respiration or pulsation, since e.g. the shape of the tumor has slightly changed, or since the patient's resting position is slightly changed. For subsequent treatment e.g. by radiation, however, the current position of the object or tumor should be determined without the need to make a 4D CT.

According to an aspect of the invention, digital tomosynthesis (DTS) is used to register the patient or to obtain the current position information of the object or tumor moving within the body or patient, especially to determine the position of the object for a specific moving or respiratory state.

Digital tomosynthesis is a limited angle method of image reconstruction. A sample of protection images is used to reconstruct image plains through the object of choice. The back projection of the projection images on the tomographic image plane yields an accumulated destination image. Objects not located close to the tomographic plane will be blurred in the image, but objects like a tumor, which are located in the isocenter of the machine, will be intensified.

In general, a digitally captured image is combined with the motion of the tube or detector as performed in conventional radiographic tomography. Contrary to CT, where the source or detector makes a complete 360 degree rotation about the object, to obtain a complete set of data from which images may be reconstructed, only a small rotation angle, such as for example 5 or 40 degrees, with a small number of discrete exposures, such as for example 10, are used for digital tomosynthesis. This incomplete set of data can be digitally processed to yield images similar to conventional tomography with a limited depth of field. However, because the image processing is digital, a series of slices at different depths and with different thicknesses can be reconstructed from the save acquisition, thus saving both time and radiation exposure.

Since the body is moving during image acquisition, motion artefacts are generated. According to the present invention, these artefacts can be avoided.

The current state of respiration during image acquisition is recorded using for example the above-mentioned IR markers attached to the surface or a part of the surface of the object or patient moving due to e.g. respiration.

Figure 2A:
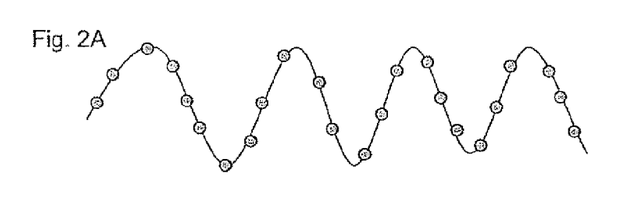
FIGS. 2A to 2C show a respiratory curve being divided into respiratory states.
Figure 2B:
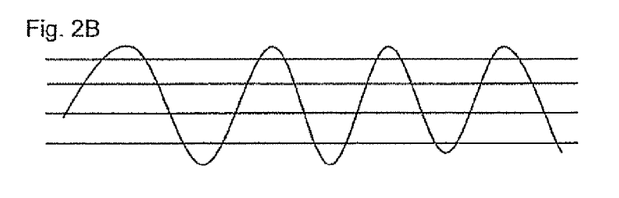
Figure 2C:
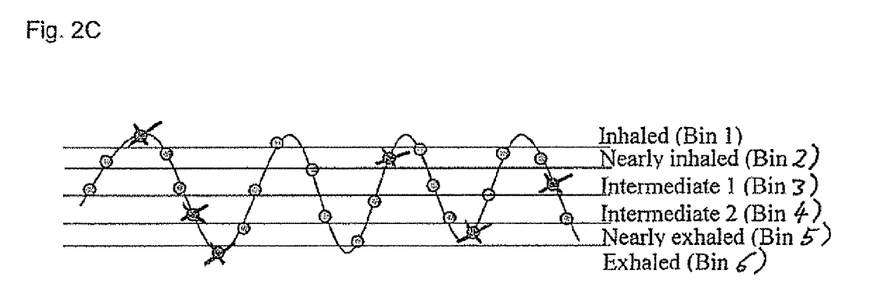

Each periodic or almost periodic movement or motion, such as respiration or pulsation, is divided into sections, such as e.g. respiratory states, as shown in an embodiment in FIG. 2. The respiratory state can be for example: inhaled, nearly inhaled, intermediate, nearly exhaled and exhaled. However, a coarser or finer division of the periodic signal or IR-respiratory curve can also be used.

Cone-beam computed tomography (CBCT) is a data acquisition method being able to provide volumetric imaging, which allows for radiographic or fluoroscopic monitoring throughout a treatment process. Cone-beam CT acquires a series of projections or images over at least a part of or the entire volume of interest in each projection. Using well-known reconstruction methods, the 2D projections can be reconstructed into a 3D volume analogous to a CT planning data set.

According to the present invention, cone-beam CT raw images are taken preferably from different direction or angles, while the position of the camera or sensor and the time of the respective image acquisition is recorded and correlated to a movement signal, such as the IR-respiratory curve. Thus, it is known for every acquired image to which movement or respiratory state it belongs and from which direction it was taken. After recording several images together with this time and position information, it is analyzed for every movement or breathing state from which direction or angle or range of angles the most images have been taken. In other words, it is determined for e.g. a pre-segmented division of all possible acquisition angles, in which segment the largest number of images has been taken.

Using this accumulation of images taken from different angles lying within a predefined segment or within a pre-defined range of angles, digital tomosynthesis (DTS) is computed to obtain a DTS-image of the object of interest.

It is possible to additionally consider images from the segment opposing the segment with the most images for improving the generated DTS image. It will be understood that the data of the opposing segment has to be mirrored to be used as additional data for improving the DTS-image.

Additionally, at least one further image being preferably taken under a different angle, such as perpendicular to the calculated DTS-image, can be taken into account for the same respiratory state. Thus, the 3D shape or position of the object of interest or tumor can be calculated. For example, if the main direction of the motion of the object is the same or close to the viewing direction of the reconstructed DTS image, it is quite difficult to obtain accurate registration results. However, if a further image is taken into account which image is taken from a different viewing angle, such as plus or minus 90 degrees, registration is quite simple.

Preferably tomographic images are computed for multiple or all respiratory states.

Using the known or recorded camera parameters of every tomographic image, such as the angle of bisector, and the segmentation data of the corresponding respiratory state (e.g. from a prior 4D CT), hereinafter referred to as "bin", the shape of the target can be computed and can be super-imposed on the image.

Small deviations can be compensated for using an intensity-based registration to obtain an accurate position of a target in every tomographic image, thus yielding an updated trajectory. In other words, the current position of an object or tumor at a specific time or breathing cycle can be calculated using e.g. an earlier taken segmented 4D CT and several DTS images, which eliminates the need for a further CT. Thus, the trajectory of a tumor can be updated.

The invention relates further to a computer program, which, when loaded or running on a computer, performs at least one of the above described method steps. Furthermore, the invention relates to a program storage medium or computer program product comprising such a program.

An apparatus for determining the position of an object moving within a body comprises a tracking system, such as an IR tracking system, which can detect the position of external markers fixed to at least part of the surface of the moving body; and comprises a camera being e.g. an x-ray detector which can be moved with respect to the body, preferably partly or fully around the body, the camera and the tracking system being connected to a computational unit correlating the marker signals being movement signals obtained by the tracking system and the camera signals including the image data and image parameters comprising at least the time the image has been taken and the position of the camera at the time the image was taken, the computational unit determining a segment or viewing range within or from which the most images were taken and elects this segment for image reconstruction, preferably by DTS.

According to a further aspect the invention relates to a treatment method using the position or trajectory of the object to be treated determined by the above described method, for controlling and/or guiding a radiation source, especially controlling and guiding the position of the radiation source from which the body or object is irradiated together with switching the radiation source on and off depending on the state of the object or body, especially the position of the object within the body, preferably considering the position of other objects which should probably not be irradiated.

According to a further aspect, the invention relates to the matching of image sequences, preferably for respiration state detection, which can be used in extracranial radiosurgery. For extracranial radiosurgery the motion of a body, such as e.g. the respiratory motion, has to be considered, since this motion may cause a tumor to shift its position by more than 1 cm. Without compensating this motion, it is unavoidable to enlarge the target volume by a safety margin, so that also healthy tissue is effected by radiation and therefore lower doses must be used to spare healthy tissue.

A method to compensate for this motion is gating which means that the irradiation beam is switched off each time the target moves out of a predefined window. The movement of the target or tumor can be determined using data of a sensor or camera, such as infrared tracking, to obtain information about the movement of the body, e.g. the respiratory curve of a patient.

A further method to compensate for this motion is chasing, where the source of radiation is actively tracked or moved so that the irradiation beam is always focussed on the object or target.

A method for determining the state of a moving body, such as the respiratory or pulsation state of a patient, which moves permanently and/or periodically, includes acquiring an image sequence, which can be an x-ray image sequence. This image sequence is compared to a prior taken sequence, such as a 4D CT scan, to determine the state of the body. Thus, the position or trajectory of the object or tumor correlated to the movement cycle or breathing state can be calculated.

The 4D CT scan can be segmented and/or otherwise analyzed, so that for each scan or dataset of the 4D CT the state, such as the respiratory state, is known.

If it can be determined to which prior taken scan or dataset the image sequence corresponds, the moving state or respiratory state corresponding to the respective image sequence or the respective images being part of the image sequence is known.

If just a single image or shot is taken and this single image should be compared to a previously taken sequence to determine the respiratory state, the image found to best match one image or shot in the previous taken image series is probably an image not having the same respiratory state as the found "matching" image.

The reason is that single images taken during free-breathing do not differ that much and the comparison of a single image to images of a series is quite complicated and does not necessarily provide the desired result.

If, however, the later taken image sequence(s) are compared as sequence (and not as individual pictures) with the previously taken image sequence, which is possible if the previously taken and later taken image sequence is taken with the same frequency, a whole sequence can be taken into account, thus eliminating the need to find a match for just one single shot in a series of previously taken images.

According to an embodiment of the invention, the frequency used for taking the image sequence or image sequences is preferably the same or close to the frequency of the previously taken images or datasets, such as the previously taken 4D volume scan. Using the same frequency provides the advantage that the whole sequence of images can be taken into account to compare this image sequence with the previous taken sequence.

Considering for example breathing motion, there are basically two indicators: the ribcage and the diaphragm.

It is obvious that the term "same frequency" should be understood to also cover (integer) multiples of the imaging frequency of one image series. If for example the prior taken image series is taken with the frequency $2*f_0$ and the later taken image sequence is taken with the frequency $f_0$, then the comparison can be made between the later taken image series and the first taken image series while leaving out every second picture of the first taken image series.

In general, it is not essential that the frequency has to be the same, as long as the time or time differences between the respective images of one image series is known, so that the respective single images of each image series can be compared to probably corresponding images of a different image series having basically the same or a similar time difference in between.

If an image series of two-dimensional images is compared to a series of 3D images, such as a 4D CT, then a reconstruction can be performed to obtain 2D images out of the 3D image series. A well-known method for obtaining radiographs out of a 3D CT-scan is to use digital reconstructed radiographs (DRR), which DRRs can be compared to the probably later taken image series.

It is noted that the later taken image series does not necessarily have to be taken from the same point of view or angle, as long as this imaging parameter, i.e. the direction from which the image is taken, is known and recorded. Using this positional information of the camera or sensor, the corresponding DRR can be calculated from each 3D data volume.

According to a further aspect, the invention provides a method for determining the way of treatment of an object within a moving body, preferably by radiation therapy or radiosurgery.

A dataset, such as a 4D CT, is provided, which is preferably segmented and includes information about the region of interest which can include information about a target volume and information about organs at risk which should not be affected by the treatment and should for example not be irradiated by using radiation therapy as treatment method.

The position and/or orientation of the regions of interest are analysed in every bin which enables the system to provide guidance to the user.

A possible guidance can be a recommendation concerning the type of treatment, i.e. whether or not gating and/or chasing is recommended.

A further recommendation can include an indication which bins should be used for the treatment. Based on the relative position and/or orientation of the planning target volume and one or more critical regions or organs at risk, specific bins can be elected for treatments, whereas other bins can for example be sorted out, if an organ at risk is closer to the planning target volume than a predefined safety distance, so that no therapy or irradiation is performed during that bin.

It is possible to combine two bins to a "treatment bin" if these two or more bins do not differ regarding a specified criterion, e.g. the distance between the planning target volume and an organ at risk.

It is possible to generate further synthetic bins using known techniques such as morphing or interpolation to generate e.g. a bin "intermediate", if only data is available for the respiratory state "inhaled" and "exhaled". If more bins are created; a more accurate 4D dose distribution can be calculated and used for treatment.

DETAILED DESCRIPTION OF PREFERRED EMBODIMENTS

Figure 1:
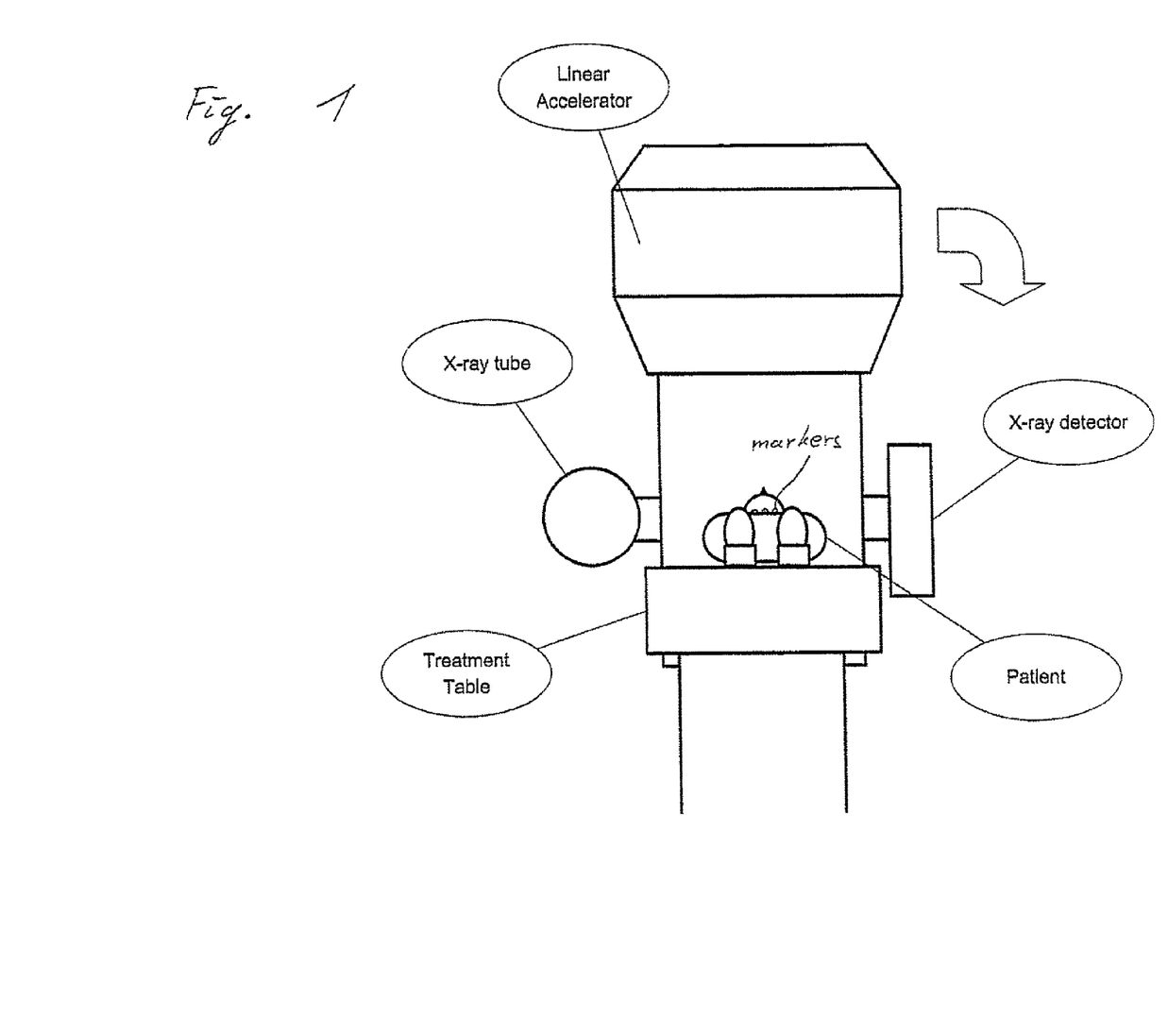
FIG. 1 is a diagram illustration of a device used for radiotherapy controlled according to the invention.

As shown in FIG. 1, a patient is positioned on a treatment table. An irradiation device, such as a linear accelerator, can be moved with respect to the patient. An x-ray source being positioned on one side of the patient emits x-rays in the direction of an x-ray detector positioned on the opposing side to obtain 2D images of a region of interest of the patient. The x-ray source and the x-ray detector can be connected to the beam source or linear accelerator or can be movable independent thereof.

As shown in FIG. 1, external markers, such as reflecting spots, are connected or sticked to the surface, such as the chest, of the patient. The reflections of the external markers can be detected by a tracking system, which generates as an output a respiratory curve as shown in FIG. 2.

FIG. 2A shows a respiratory curve generated from a sequence of images referred to as sample points.

As shown in FIGS. 2B and 2C, the respiratory curve can be segmented into several different states, being for example inhaled, nearly inhaled, intermediate 1, intermediate 2, nearly exhaled and exhaled.

By moving the x-ray detector shown in FIG. 1 relative to the patient, a series of images is taken, wherein the position of the x-ray detector and the time at which the respective image is taken is recorded. Using the information from the respiratory curve acquired simultaneously with the image acquisition by the x-ray detector, a series of images taken from different positions or angles can be collected or stored for each respiratory state.

Figure 3A:
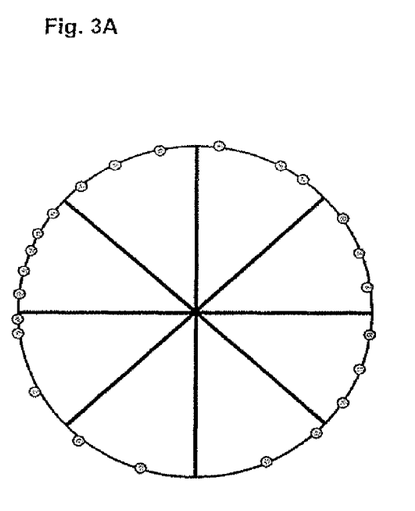
FIGS. 3A to 3C illustrate methods for DTS image reconstruction
Figure 3B:
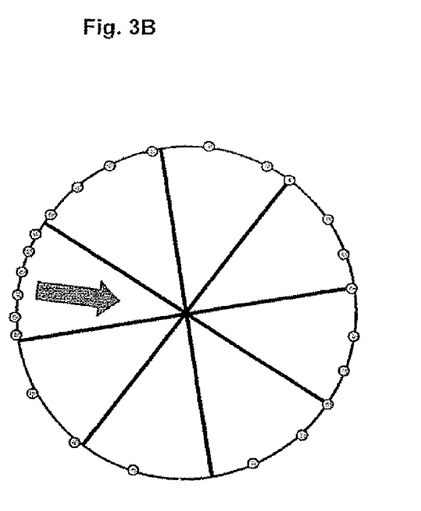
Figure 3C:
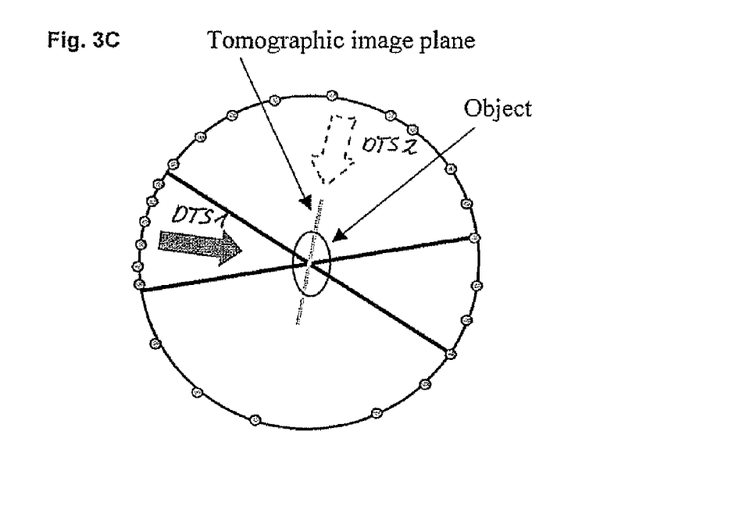

FIGS. 3A to 3C show as an exemplary embodiment the respiratory state "nearly inhaled", where a series of images is taken under respective different angles at the same or at later or earlier respiratory states "nearly inhaled" of a different cycle during some full breathing cycles. The circle representing a 360 degree angle corresponding to the camera position as shown in FIG. 3A is divided into 8 segments. After the image acquisition with the x-ray detector is finished, it is determined in which of the 8 segments the biggest accumulation of images being shown as small circles is.

FIG. 3B shows the determined segment found to include the largest number of images being the segment from which the DTS is computed in the next step. The plane perpendicular to the bisector of the selected segment is the plane of the tomographic image to be computed, as shown in FIG. 3C.

Thus, tomographic images can be computed for multiple respiratory states by repeating the steps explained with reference to FIG. 3 for every single respiratory state. Using the known camera parameters of every tomographic image (angle of bisector) and the segmentation data of the corresponding respiratory state (bin), the shape of the target can be computed and can be superimposed on the image. Deviations can be compensated for using an intensity-based registration to obtain the accurate position of the target in every tomographic image. Preferably intensity-based registration includes only a rigid transformation. However, it is also possible to perform an elastic registration.

To ensure robust registration results, a second tomographic image, perpendicular to the existing one, can be taken into account for the same respiratory state, as shown in FIG. 3C with the arrow DTS 2. For example, if the main direction of tumor motion is the same as the viewing direction of the reconstructed DTS image, it will be very difficult to get accurate registration results. But if a further image taken from another viewing angle (e.g. +90 degrees) is taken into account, this problem can be solved, so that 3D information is obtained.

Figure 4:
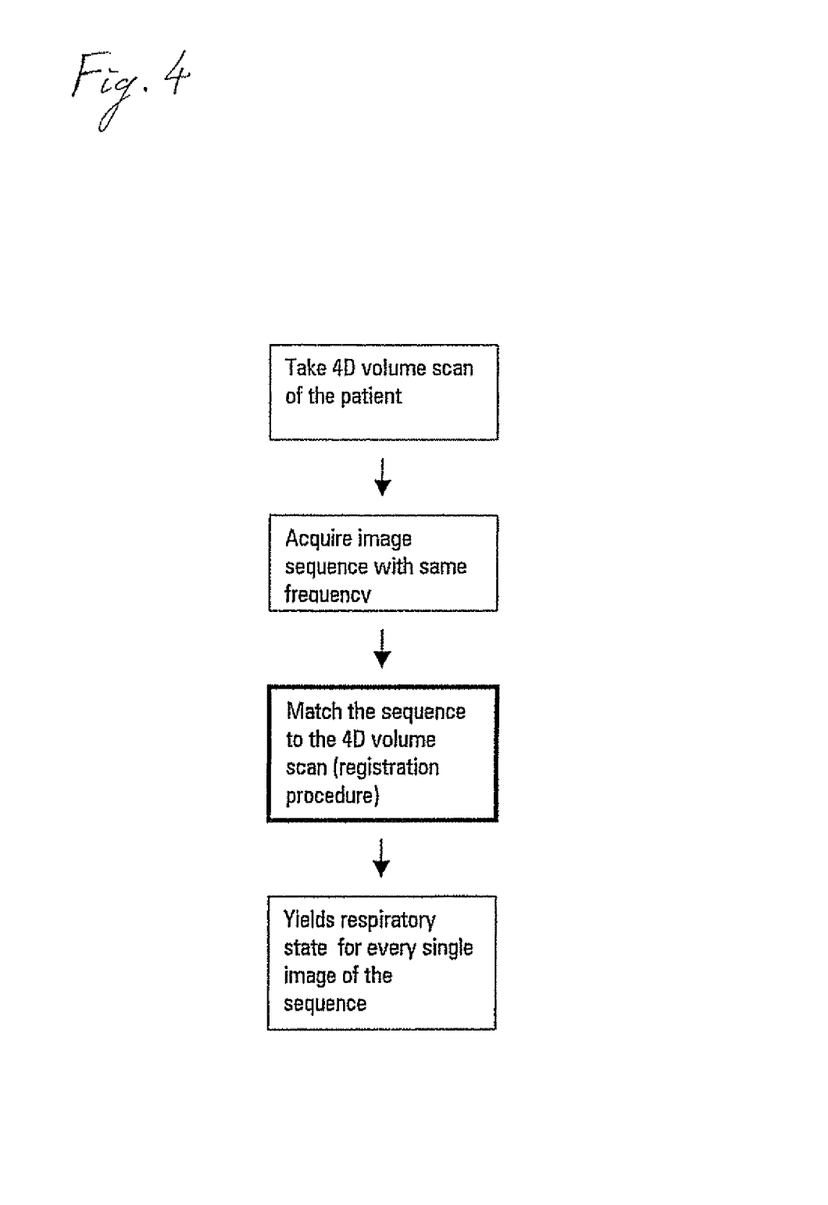
FIG. 4 is a flowchart illustrating a method for determining the respiratory state.

FIG. 4 shows a registration procedure to match a sequence of 2D images to a previously recorded dataset, such as a 4D volume scan of a patient.

According to the shown embodiment, the 2D image sequence is acquired with the same frequency, so that the sequence can be matched to the 4D volume scan, as explained hereinafter with reference to FIG. 5.

If the time span of an average respiratory cycle of a specific patient is for example about five seconds and a 4D volume scan consists of 8 bins, the images of the sequence should be taken every (5000 ms/(8×2−1))=333 ms.

Figure 5A:
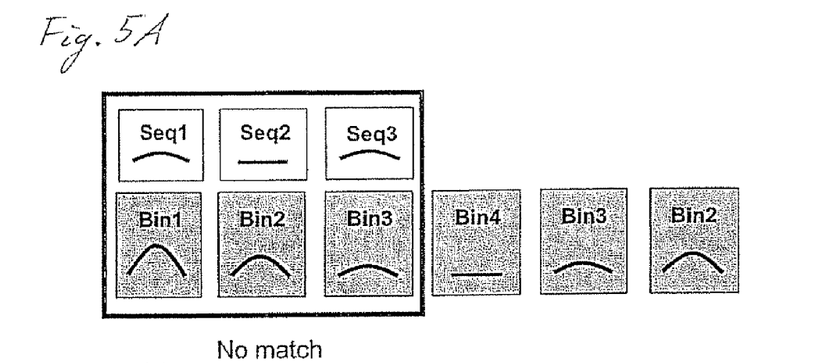
FIGS. 5A to 5C illustrate a registration procedure performed according to an embodiment of the invention.
Figure 5B:
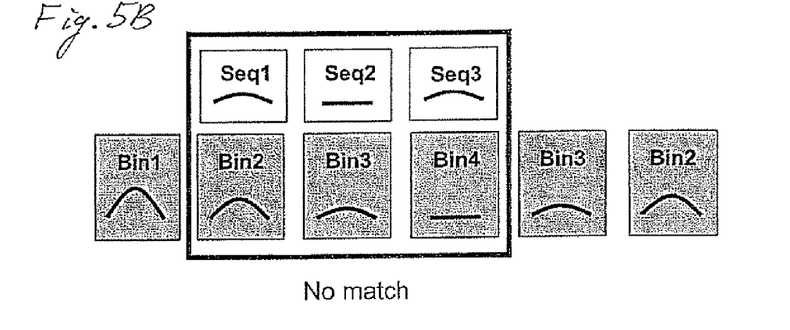
Figure 5C:
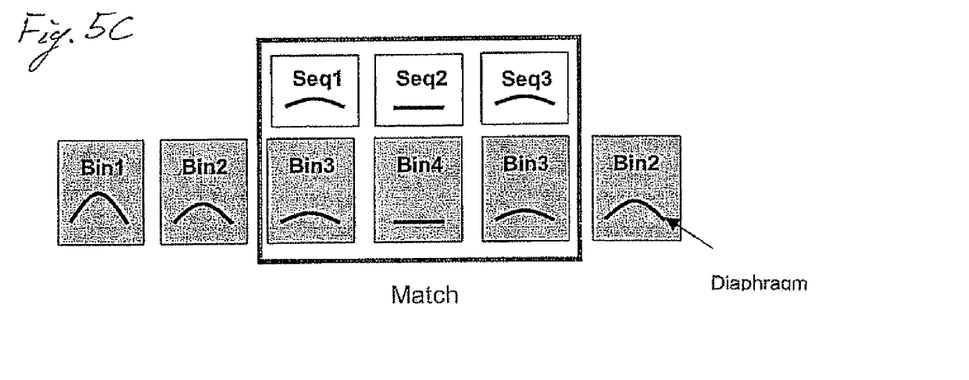

FIG. 5 shows the registration method for matching the 2D image sequence Seq 1, Seq 2, Seq 3 to the 4D CT sequence Bin 1, Bin 2, Bin 3, Bin 4, Bin 3, Bin 2, . . . .

The bold line shown below the respective designation of the sequence or Bin should symbolize the state of the diaphragm being a possible indicator for the respiratory state.

As can be seen in FIGS. 5A and 5B, there is no match between the respective sequence and the bins. The sequence is shifted with respect to the bins until a match is reached, as shown in FIG. 5C.

The registration is preferably performed 2D to 2D, i.e. a pre-generated DRRs shall be matched to n images of the sequence. The accumulate similarity measure values shall be optimised and the best match sorts the images of the sequence to the respiratory states of the 4D volume scan.

Similarity measures are known from the above mentioned K. Berlinger, "Fiducial-Less Compensation of Breathing Motion in Extracranial Radiosurgery", Dissertation, Fakultät für Informatik, Technische Universität München; which is included by reference. Examples are Correlation Coefficients or Mutual Information.

When using stereo x-ray imaging, this procedure can be performed twice, i.e. for each camera, to further enhance the robustness by taking into account both results.

Preferably, the two x-ray images of the pair of x-ray images are perpendicular to each other and are taken simultaneously. To perform the 2D/4D registration, several independent 2D/3D registration processes using e.g. DRRs can be performed. Both x-ray images are successively matched to all bins of the 4D CT and the best match yields the respiratory states.

As shown in FIG. 2A, the images of the sequence and their position in time of the corresponding respiratory curve is depicted. The respiratory curve from IR is used to select one image per treatment bin (respiratory state) and to sort the images by the respiratory state, as shown in FIG. 2C. All points on the respiratory curve are sample points where an x-ray image has been taken. The sample points marked with an "x" additionally serve as control points for segmenting the trajectory computed afterwards.

Figure 6:
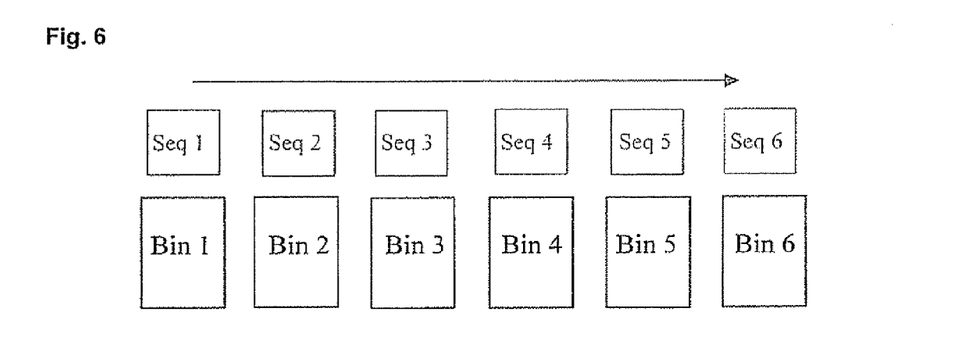
FIG. 6 shows the matching of a sequence to treatment bins.

The sequence is matched to the treatment bins, as shown in FIG. 6. The images of the sequence are moved synchronously over the treatment bins (DRRs) and the accumulated similarly measure is optimised.

The result sorts every single image to a bin and therefore to a respiratory state. The isocenters of the bins serve as control points of the trajectory, i.e. the isocenters were determined in the planning phase.

If no 4D CT is available (3D case), the planning target volume (PTV) can be manually fitted to some well distributed single images. In the 3D and 4D case, the contour of the PTV can be interpolated geometrically over all images of the sequence.

Figure 7A:
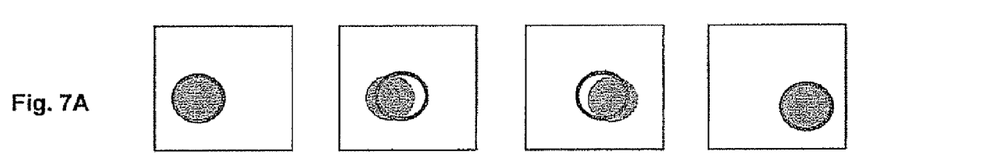
FIGS. 7A to 7C show the fine adjustment using intensity-based registration.

FIG. 7A shows an example, where the first and the last contour match is known and between these images the interpolation is performed, yielding an approximate match.

Fine adjustment using intensity-based registration can be performed for every single image, so that no sequence matching is performed.

Figure 7B:
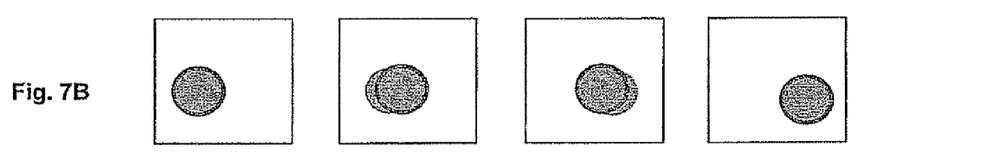

FIG. 7B shows that the intensity of the target is now taken into account.

Figure 7C:
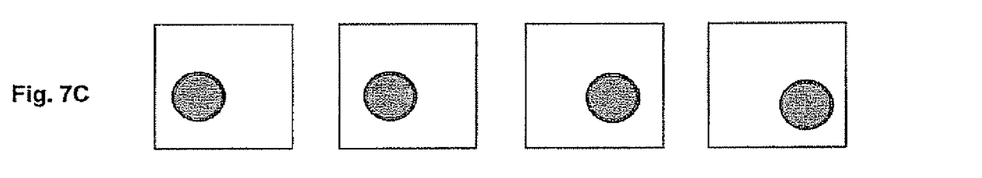

FIG. 7C shows the thereby reached perfect match.

Finally, visual inspection can be performed by the user and if necessary manual correction can be performed.

So the position of the PTV in every single image can be determined, which can be used to define a trajectory in the next step.

Figure 8:
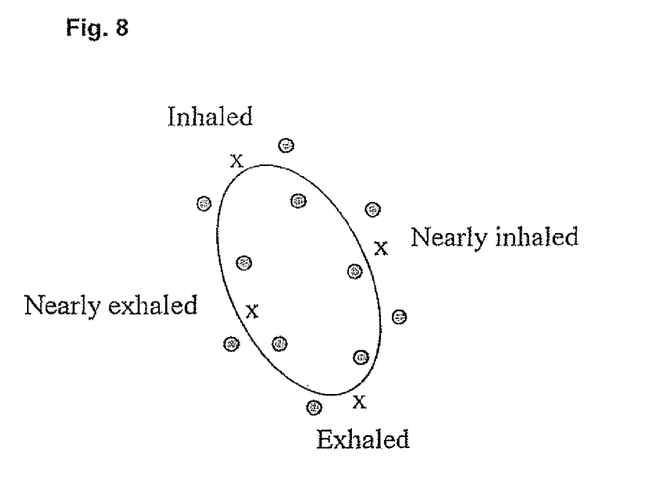
FIG. 8 shows the fitting of a trajectory through sample point.
Figure 9:
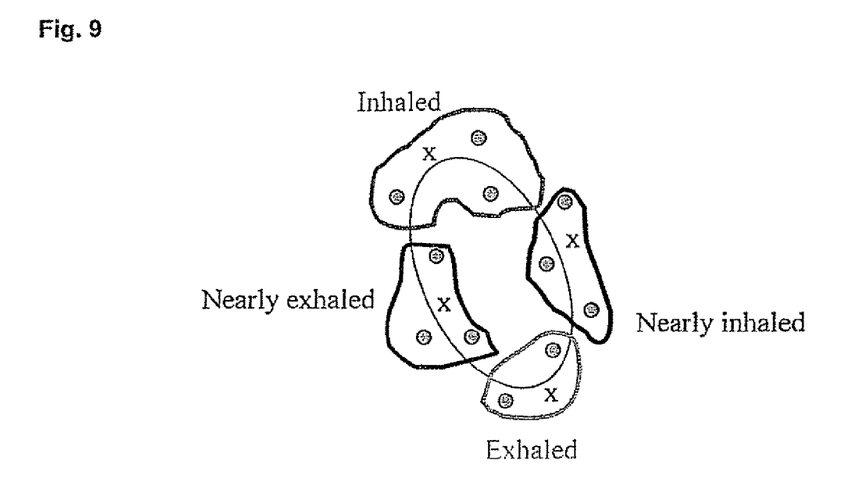
FIG. 9 shows the segmentation of the trajectory of FIG. 8 into treatment bins.
Figure 10A:
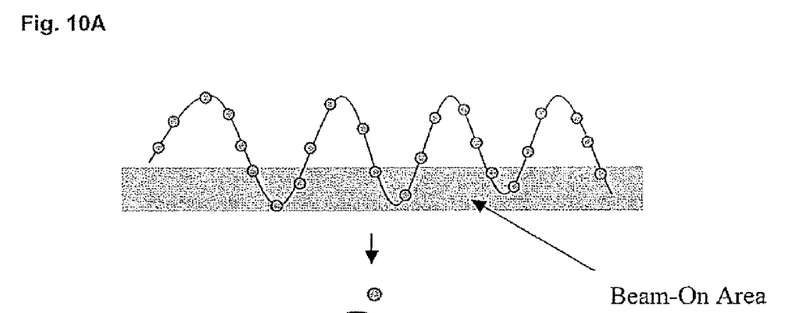
FIGS. 10A and 10B illustrate the generation of treatment parameters.
Figure 10B:
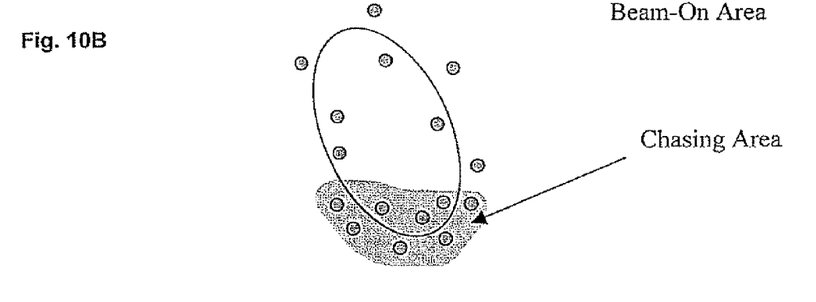

For generating the parameters for treatment (4D), a trajectory is fitted through the sample points, as shown in FIG. 8, and the control points are used, wherein the trajectory is divided into (breathing phase) segments, as shown in FIG. 9.

Images located between two control points (marked as 'x' in FIGS. 8 and 9), are sorted to a respiratory state or control point by matching these to the two competing bins. The image is assigned to the best matching control point. After this sorting procedure is completed, the segments can be determined as visualized in FIG. 9. Each segment stands for a specific respiratory state and therefore treatment bin.

To assist in the adding of trajectory segments to a chasing area (the chasing area is the area where the beam actually follows the target, outside this area the beam is switched off (gating)), the standard deviation from sample points of a specific segment to the trajectory taking into account the relative accumulation should be minimized. It is advantageous to find the most "stable" or best reproducible trajectory or trajectories to be used for later treatment by irradiation. Having determined the best reproducible trajectories, the treatment time can be minimized since the beam can be quite exactly focussed while largely sparing out healthy tissue.

Regions neighboring critical bins (segments) are omitted
User control:
  Visualization of DRR of specific bin with organs at risk (OAR) and isodoses drawn in
  Treatment time
  Expected positioning deviation (how "reproducible" is a trajectory)

For generating the parameters for treatment (3D) the following steps are performed:
  Fitting of trajectory through sample points
  Definition of beam-on area in IR respiratory curve
  Computation of trajectory segment (chasing area) based on sample points located in the beam-on area (see FIG. 10)
  Display of trajectory segments with high standard deviations
  Display of expected treatment time
  Display of the selected trajectory segment
  Manual readjustment to optimize treatment time, standard deviations and chasing area
  Automatical determination of the isocenter (sort of reference isocenter with respect to chasing trajectory)
  If necessary, export to treatment planning system (TPS) for plan-update The treatment in the 3D and 4D case have as input:
Gained correlation of IR-signal and trajectory segment(s)
Isocenter
Procedure:
  Positioning of the determined patient isocenter to the machine isocenter
  Continuously recording of IR-signal and transferring the signal into position on the trajectory
  Within the segment to treat: chasing; outside: gating
  Use gating (beam off) if an error occurs in the above computations, e.g.:
    IR marker is not visible
    Changed pattern of the marker geometry
    No corresponding trajectory position to current signal in correlation model
  It is possible to take verification shots
    Based on trajectory position drawing in of the planning target volume (PTV) to enable a visual inspection and if necessary an intervention
  It is possible to continuously take images during treatment (yields sequence with lower frequency)
    To document treatment
    To permanently check and update trajectory automatically
    Export information to TPS for possible plan-update
Error handling, e.g. during treatment, can have as input:
old image sequence
new image sequence
Procedure:
A) Displaced respiratory curve/Unchanged trajectory
  i. Registration of old and new sequence (Algorithm can be close to that described with reference to FIGS. 2C and 6, but instead of the DRR sequence the old sequence is used)
  ii. Showing tumor positions of old sequence in new one
    ⇨ PTV matches to new images
    ⇨ Correlation between IR-Signal and trajectory will be updated
B) Changed trajectory
  i. Registration of old and new sequence (see above)
  ii. Automatic detection if an update is necessary: indicator is a towards inhalation falling similarity measure value (see e.g. K. Berlinger, "Fiducial-Less Compensation of Breathing Motion in Extracranial Radiosurgery", Dissertation, Fakultät für Informatik, Technische Universität München; section 2.3.3)
    ⇨ Automatic image fusion (image to image, not whole sequence as described when generating the sample points of the treatment trajectory) to get updated tumor positions and therefore the updated trajectory.

Incremental Setup of Gating and/or Chasing (for Example Treatment on a Different Day)
A) First fraction: as described so far, the DRR sequence generated from the treatment bins is used for the initial sequence matching (as described when generating the sample points of the treatment trajectory; FIGS. 2C and 6).
B) Later fractions: instead of the DRR sequence, the sequence of the last fraction can be used for the initial registration procedure.

For a plan-update the following can be done:
A) Recommended trajectory segment (chasing area) is different from initially planned bin (when using 4D-CT a bin is equivalent to a trajectory segment)
  a. Selection of the recommended bin for treatment b. Planning of new beam configuration taking into account changed relative position and orientation of PTV and OARs to each other B) Update of the planned dose distribution a. Detection of the actual PTV position in the control images using intensity-based registration (as described when generating the sample points of the treatment trajectory)

b. Computation of the dose distribution actually applied to the target c. Taking these results into account, update the beam configuration in a way to reach the originally wanted dose distribution Image subtraction can be performed to enable a detection of the tumor in every single verification shot. Thus, there is no need for using implanted markers anymore. An initially taken image sequence of the respiratory cycle forms the basis of this approach. The thereby gained information is stored in an image mask. Applying this mask to any new verification shot yields an image which emphasizes the contour of the tumor. The moving object is separated from the background.

There are two ways to generate the mask

1. Compute a mean image of the sequence by averaging the pixel values of the sequence. That means for every pixel of the destination image:

$$I_{Mask}(x, y) = \frac{1}{n}\sum_{i=1}^{n} Seq_i(x, y)$$

The average image has to be subtracted from the verification shot to obtain the image with emphasized target contour.

2. Compute a maximum image of the sequence. That means for every pixel of the destination image:

$$I_{Mask}(x,y) = MAX_{i=1}^{n}(Seq_i(x,y))$$

In this case the verification shot has to be subtracted from the maximum image to obtain the image with emphasized target contour.

Figure 11:
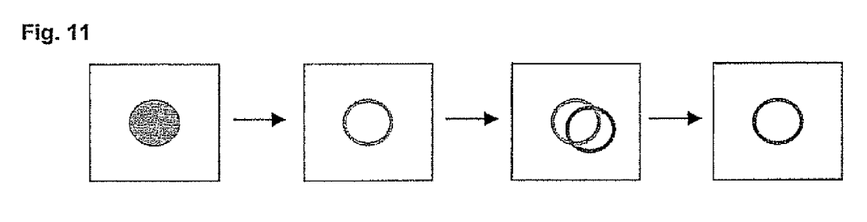
FIG. 11 shows the contour-based detection of a planning target volume.

For contour-based PTV detection, as shown in FIG. 11, the known contour of the target and an x-ray image containing the target is used as input. The procedure includes the steps:

Applying an edge detector to the X-ray image (e.g. Canny Edge)

Matching of the contour to the edge image

Optimize similarity measure value

Cone-Beam Raw-Data can be used for Sequence Generation having as input raw images of Cone-Beam imaging with known camera position; and the infrared signal. An image sequence with known respiratory states can be obtained: Images are not located in the same plane, but with the known camera parameters this sequence can be matched to a 4D CT, as described when generating the sample points of the treatment trajectory. Furthermore, the Cone-Beam volume is received as output.

Cone-Beam of moving objects can have as input raw images of Cone-Beam imaging with known camera position; and expected position of PTV for every raw image (e.g. based on 4D CT scan and IR signal during Cone Beam acquisition).

As output the reconstructed Cone Beam dataset can be obtained.

The advantage of this reconstruction method is to properly display an object that was moving during the acquisition of the raw images.

Figure 12A:
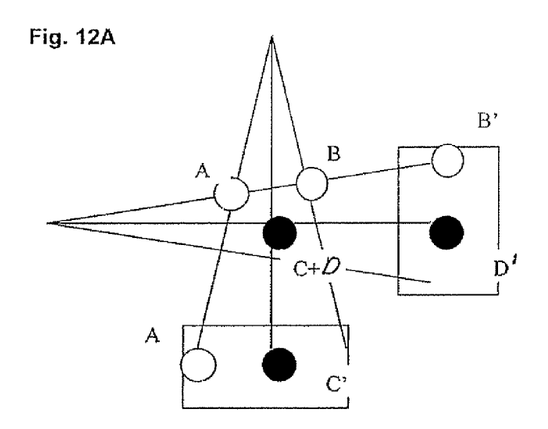
FIGS. 12A to 12C illustrate the reconstruction of object data.

During the acquisition of Cone Beam raw images the objects are projected to the raw images. In FIG. 12A below the non-moving object (black circle) is at the same position C+D during the acquisition of two raw images. It is projected to position C' and D' on the raw images. Another object (hollow circle) moves during acquisition. It is a different position A and B during acquisition of the two raw images. It is projected to position A' and B' in the raw images.

Figure 12B:
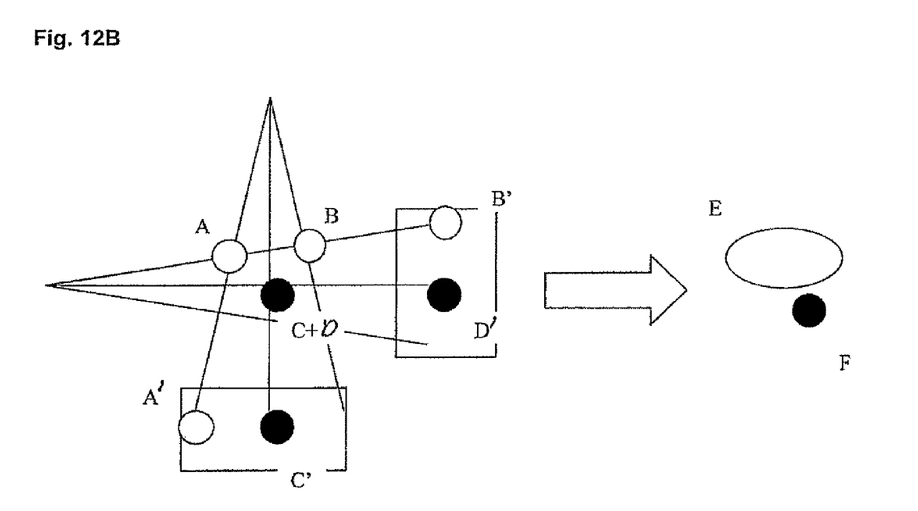

During a conventional reconstruction, a mathematical algorithm solves the inverse equation to calculate the original density of the voxels. For non-moving objects like the filled black circle in FIG. 12B, the reconstruction result is of sufficient quality. If the object moves during acquisition of the raw images, the reconstruction quality is degraded. The object at position C' and D' is properly reconstructed to position C+D in the voxel set. Accordingly the Cone Beam data set will display the black circle (F). The hollow circle at positions A' and B' in the images is not properly reconstructed because position A and B differ. The voxel set will show a distorted and blurred object E.

Figure 12C:
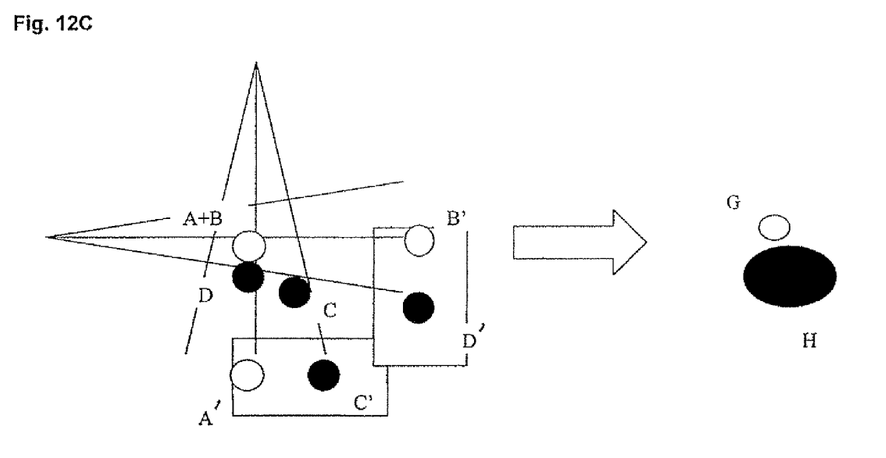

The new reconstruction algorithm shown in FIG. 12C takes the position C+D during acquisition into account. It calculates the projection parameters of the Object (hollow circle) to the raw images. These parameters depend on the object's position during acquisition of the images. By doing this the beams through the object on the raw images (A' and B') will intersect at the corresponding voxel in the Cone Beam data set (A+B)). The object is reconstructed to the correct shape G. Instead the stationary object is now distorted to the shape H.

The invention claimed is:

1. A non-transitory computer-readable storage medium on which a program is stored which, when running on a computer of an associated medical treatment apparatus, causes the computer of the associated medical treatment apparatus to perform a method for determining a treatment plan to be used for selective delivery of a therapeutic treatment beam to an anatomical body part moving in a body of an associated patient due to a breathing motion of the associated patient, the method comprising:

operating the associated medical treatment apparatus at a first imaging frequency to obtain a first dataset describing a first sequence of images describing the anatomical body part of the associated patient which have been taken at different first times during the moving of the body part due to the breathing motion of the associated patient at the different first times, wherein the first imaging frequency defines a first cycling rate of an image acquisition beam directed at the anatomical body part during the breathing motion of the associated patient at the different first times, wherein the first sequence of images comprises a first plurality of segment bins of image sequence portions of the first sequence of images;

determining, for each segment bin of image sequence portions of the first plurality of segment bins, a different respiratory state of the breathing motion of the associated patient at the different first times;

operating the associated medical treatment apparatus at a second imaging frequency to obtain a second dataset describing a second sequence of images describing the anatomical body part of the associated patient which have been taken at different second times during a moving of the body part due to the breathing motion of the associated patient at the different second times, wherein the second imaging frequency defines a second cycling rate of the image acquisition beam directed at the anatomical body part during the breathing motion of the associated patient at the different second times, wherein the second sequence of images comprises a second plurality of segment bins of image sequence portions of the second sequence of images, each segment bin of image sequence portions of the second plurality of segment bins corresponding to a different unknown respiratory state of the breathing motion of the associated patient at the different second times, wherein the second imaging frequency is an integer multiple of the first imaging frequency;

determining, by the processor, a match between two or more of the first plurality of segment bins of image sequence portions described by the first dataset and two or more of the second plurality of segment bins of image sequence portions described by the second dataset;

assigning the determined respiratory state of the two or more of the first plurality of segment bins to the two or more of the second plurality of segment bins matching the two or more of the first plurality of segment bins;

determining, by the processor, the treatment plan to be used for selective delivery of the therapeutic treatment beam to the anatomical body part during the second times in accordance with the assigned determined respiratory states; and generating, by the processor, an output signal representative of the determined treatment plan, the output signal being operative to control an associated source of the therapeutic treatment beam for the selective delivery of the therapeutic treatment beam to the anatomical body part of the associated patient during the different second times based on the treatment plan.

2. The storage medium according to claim 1, wherein the second dataset is shifted with respect to the first dataset in time to determine a correlation or matching value as the match.

3. The storage medium according to claim 1, wherein the first dataset is a 4D computer tomography (4D CT) dataset.

4. The storage medium according to claim 3, wherein a digital reconstructed radiograph (DRR) is reconstructed from each three-dimensional dataset of the 4D CT dataset.

5. The storage medium according to claim 1, wherein, when running on the computer, the program stored on the storage medium causes the computer to perform a further step comprising:

assigning each of the plurality of segment bins of images to a different state of the breathing motion of the associated patient.

6. The storage medium according to claim 1, wherein, when running on the computer, the program stored on the storage medium causes the computer to perform a further step comprising:

operating the associated medical treatment apparatus to generate, in accordance with the treatment plan, the therapeutic treatment beam for the selective delivery of the therapeutic treatment beam to the anatomical body part of the associated patient.

7. A medical treatment apparatus for determining a treatment plan to be used for selective delivery of a therapeutic treatment beam to an anatomical body part moving in a body of an associated patient due to a breathing motion of the associated patient, the medical treatment apparatus comprising:

a processor;

an imaging device operable by the processor of the medical treatment apparatus at a first imaging frequency to obtain a first dataset comprising a first sequence of images representative of the anatomical body part of the associated patient which have been taken at different first times during the moving of the body part due to the breathing motion of the associated patient at the different first times, wherein the first imaging frequency defines a first cycling rate of an image acquisition beam directed by the imaging device at the anatomical body part during the breathing motion of the associated patient at the different first times, wherein the first sequence of images comprises a first plurality of segment bins of image, sequence portions of the first sequence of images;

determining, for each segment bin of image sequence portions of the first plurality of segment bins, being a different respiratory state of the breathing motion of the associated patient at the different first times;

wherein the imaging device is operable at a second imaging frequency to obtain a second dataset comprising a second sequence of images representative of the anatomical body part of the associated patient which have been taken at different second times during a moving of the body part due to the breathing motion of the associated patient at the different second times, wherein the second imaging frequency defines a second cycling rate of the image acquisition beam directed by the imaging device at the anatomical body part during the breathing motion of the associated patient at the different second times, wherein the second sequence of images comprises a second plurality of segment bins of image sequence portions of the second sequence of images, each segment bin of image sequence portions of the second plurality of segment bins corresponding to a different unknown respiratory state of the breathing motion of the associated patient at the different second times, wherein the second imaging frequency is an integer multiple of the first imaging frequency;

a non-transient memory device storing the first and second datasets;

wherein the processor is operative to determine a match between two or more of the first plurality of segment bins of image sequence portions described by the first dataset and two or more of the second plurality of segment bins of image sequence portions described by the second dataset;

wherein the processor is operative to assign the determined respiratory state of the two or more of the first plurality of segment bins to the two or more of the second plurality of segment bins matching the two or more of the first plurality of segment bins;

wherein the processor is operative to determine the treatment plan to be used for selective delivery of the therapeutic treatment beam to the anatomical body part during the second times in accordance with the assigned determined respiratory states; and a source of the therapeutic treatment beam, the source being responsive to an output signal generated by the processor to selectively generate and deliver the therapeutic treatment beam to the anatomical body part of the associated patient during the different second times based on the treatment plan.

8. The medical treatment apparatus according to claim 7, wherein the second dataset is shifted with respect to the first dataset in time to determine a correlation or matching value as the match.

9. The medical treatment apparatus according to claim 7, wherein the first dataset is a 4D computer tomography (4D CT) dataset.

10. The medical treatment apparatus according to claim 7, wherein a digital reconstructed radiograph (DRR) is reconstructed from each three-dimensional dataset of the 4D CT dataset.

11. The medical treatment apparatus according to claim 7, wherein:
- the imaging device is operable by the processor at the first and second imaging frequencies to obtain the first and second datasets such that the second imaging frequency is the same as the first imaging frequency or wherein the second imaging frequency is an integer multiple of the first imaging frequency.

* * * * *